United States Patent [19]

Dockner et al.

[11] 4,105,657
[45] Aug. 8, 1978

[54] PRODUCTION OF N-ALKYL DERIVATIVES OF CYCLIC ALKYLENIMINES

[75] Inventors: Toni Dockner, Meckenheim; Herbert Toussaint, Frankenthal; Martin Decker, Ludwigshafen, all of Fed. Rep. of Germany

[73] Assignee: BASF Aktiengesellschaft, Ludwigshafen, Fed. Rep. of Germany

[21] Appl. No.: 786,116

[22] Filed: Apr. 8, 1977

Related U.S. Application Data

[63] Continuation of Ser. No. 605,238, Aug. 8, 1975, abandoned, which is a continuation of Ser. No. 330,243, Feb. 7, 1973, abandoned.

[30] Foreign Application Priority Data

Feb. 7, 1972 [DE] Fed. Rep. of Germany ....... 2205597

[51] Int. Cl.$^2$ ................... C07D 295/02; C07D 265/30
[52] U.S. Cl. .......................... 260/239 B; 260/293.51; 260/307 FA; 260/326.1; 260/326.8; 260/329 R; 260/306.7 R; 544/53; 544/88; 544/178; 548/300; 252/437; 544/404; 544/242

[58] Field of Search ........ 260/293.51, 239 B, 268 SY, 260/326.8, 585 B, 583 R, 306, 7 R, 307 FA, 326.1, 251 R, 329 R; 252/435; 544/53, 88, 178; 548/300

[56] References Cited

U.S. PATENT DOCUMENTS

| 2,073,671 | 3/1937 | Andrews | 260/585 B |
| 3,112,317 | 11/1963 | Marschall | 260/268 |
| 3,652,581 | 3/1972 | Spaenig | 260/309.2 |

OTHER PUBLICATIONS

Dockner, Chem. Abs. 80, 108532r (1974).
Shell, "Encyclopedia of Industrial Chem. Anal.," vol. 11 (1973) p. 487.
Szymanski et al., Chem. Abs. 83, 58401m (1975).

*Primary Examiner*—Donald G. Daus
*Assistant Examiner*—Mark L. Berch
*Attorney, Agent, or Firm*—Keil, Thompson & Shurtleff

[57] ABSTRACT

Production of N-alkylated cyclic alkylenimines by reaction of cyclic alkylenimines with an alcohol or ether in the gas phase in the presence of a high-area $SiO_2/P_2O_5$ catalyst.

4 Claims, No Drawings

PRODUCTION OF N-ALKYL DERIVATIVES OF CYCLIC ALKYLENIMINES

This is a continuation, of application Ser. No. 605,238 filed Aug. 18, 1975, now abandoned which is a streamlined continuation of U.S. Ser. No. 330,243 filed Feb. 7, 1973, now abandoned.

The invention relates to a process for the N-alkylation — substantially at atmospheric pressure — of cyclic alkylenimines by means of aliphatic hydroxyl compounds or ethers thereof in the presence of a catalyst having a dehydrating effect.

Various methods have been described for the N-alkylation of aliphatic heterocyclic nitrogen compounds. In Houben-Weyl Methoden der Organischen Chemie. 4th edition, volume 11/1, pages 112 et seq. a distinction is made between processes using catalysts having hydrogenating-dehydrogenating action and those using catalysts having dehydrating action.

In most cases the amines are reacted with alcohols or carbonyl compounds in the presence of hydrogenation catalysts and hydrogen at superatmospheric pressure and elevated temperature:

In Belgian Pat. No. 694,068 the reaction is carried out between morpholine and alcohols in contact with catalysts of nickel or cobalt, copper and titanium dioxide at from 150° to 300° C and at a pressure of from 35 to 350 atmospheres.

According to German patent application No. B 13,494 N-alkyl-piperidines and N-alkylpyrrolidones may be prepared by treatment of mixtures of aliphatic ketones and piperidine or pyrrolidone with hydrogen at elevated temperature and superatmospheric pressure in the presence of nickel-cobalt-copper catalysts.

J. Org. Chem., 21, 86 and 87 (1956), discloses the alkylation of piperazines with alcohols in contact with Raney nickel at 200° C. Methylation can be effected with formaldehyde and hydrogen at 50° to 90° C and a pressure of from 30 to 50 atmospheres in one stage in contact with cobalt catalysts.

It is a disadvantage of the hydrogenating methods that superatmospheric pressure, often expensive catalysts and hydrogen are necessary for carrying out the reaction.

According to Houben-Weyl, reactions over dehydrating catalysts are capable of wide use but "the literature is concerned mainly with reactants which are of little interest preparatively". Acid reacting catalysts are to be avoided. Little is known about the present problem of alkylating cyclic imines on the nitrogen atom; merely the reaction of piperidine with alcohols in the presence of aluminum oxide to form N-alkylpiperidines has been studied by Galik and collaborators (Coll. of Czechoslovak Chemical Communications, 33, 609 to 613 (1968); the yields are from 19 to 56% of theory. Aluminum oxide, phosphoric acid, aluminosilicates and other dehydrating catalysts are mainly used for the alkylation of aromatic amines (German Pat. No. 617,990 or Ind. Engg. Chem. Prod. Res. Developm., 7, 159 (1968)).

It is an object of the invention to provide a process which will enable the N-alkylation of cyclic alkylenimines with aliphatic hydroxyl compounds or their ethers to be carried out at atmospheric pressure.

We have found that this object is achieved with high yields and very good conversions by carrying out the reaction in the presence of a catalyst which consists of silicon dioxide of a specific surface area of from 50 to 500 m²/g which contains from 0.1 to 20% by weight of phosphoric acid and by carrying out the reaction in the gas phase.

Cyclic alkylenimines for the purposes of the present invention, which can be alkylated on the secondary amine hydrogen, may be represented by the general formula:

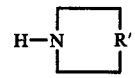

in which R' is a bifunctional radical selected from the group comprising:

saturated $C_2$ to $C_{12}$ polymethylene radicals having up to two methyl and/or ethyl substituents;

olefinically unsaturated polymethylene radicals of four to ten carbon atoms in the chain and up to two methyl and/or ethyl substituents;

$C_3$ to $C_{10}$ saturated or olefinically unsaturated polymethylene heterochain radicals of one or two nitrogen, oxygen and/or sulfur atoms inserted in the chain or

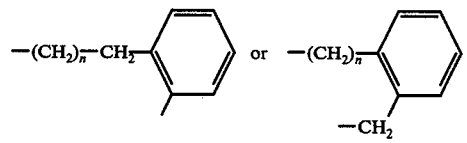

n being selected from the integers comprising 1, 2 an 3.

Examples of imino compounds suitable for the invention therefore include: ethylenimine, propylenimine-(1,3) (= azacyclobutane); five-membered ring compounds such as butylenimine (= pyrrolidine), imidazolidine, 1-methylimidazolidine, oxazolidine, thiazolidine and also five-membered ring compounds which are condensed onto an aromatic ring, as for example dihydroisoindole; six-membered ring compounds such as piperidine, 3-propylpiperidine, piperazine, N-alkylpiperazines, perhydro-(1,3)-oxazine, perhydropyrimidine, perhydro-(1,3)-thiazine and analogs thereof condensed for example with the phenylene radical, seven-membered ring compounds such as hexamethylenimine (= perhydroazepine), perhydrothiazepine and rings having a larger number of members and having imino groups, as for example decamethylenimine and its derivatives.

Morpholine, piperazine, pyrrolidine, piperidine and hexamethylenimine are preferred imines.

Suitable alcohols are saturated lower aliphatic alcohols such as particularly methanol and also ethanol, isopropanol, and suitable ethers are the corresponding dialkyl compounds.

The reaction is carried out in the gas phase and the catalyst may be present in a fixed bed or in a fluidized bed. This makes it a condition of the structure of suitable imines that they should be capable of being vaporized at the reaction temperature without decomposition. If the vapor pressure of the compounds is inadequate for complete evaporation at the reaction temperature, the compounds may also be converted into the gas phase by means for example of a carrier gas stream or at subatmospheric pressure.

The reaction temperature is generally from 150° to 350° C, preferably from 180° to 300° C. Atmospheric pressure is generally used but slightly superatmospheric or subatmospheric pressure may also be used, for example pressures of from 0.1 to 5 atmospheres.

The catalyst consists essentially of SiO$_2$ having a specific surface area of from 50 to 500 and particularly from 300 to 450 m$^2$/g and from 0.1 to 20%, particularly from 2 to 10%, by weight of phosphoric acid based on the total weight of the catalyst. When a fluidized bed is used the catalyst may be conveniently of a particle size of from 60 to 1000 microns. When a fixed bed is used the catalyst may be used in the form of spheres, pellets or irregular shapes.

The production of a suitable catalyst may be assumed to be known to those skilled in the art. A suitable catalyst may be prepared with special advantage as follows:

Commercial collodial aqueous sodium silicate solution is converted by the addition of sulfuric acid and via the intermediate stage of a silicic acid sol into a silicic acid hydrogel of high water content which is desalted (eluated) with ammoniacal water. The desalted hydrogel with the appropriate amount of phosphoric acid and with an addition of oxalic acid is treated in a mill or another apparatus producing shear forces so that peptization (liquefaction) takes place. The aqueous phase obtained is sprayed for example into a stream of smoke gas so that a particulate powder is obtained which is suitable as a fluidized bed catalyst. Silica gel pellets may be obtained by appropriate other drying methods.

The internal surface areas of the catalysts obtained may be determined for example by the known BET method.

A review of the field of the production of such catalysts is contained for example in Ullmann's Encyklopädie der technischen Chemie, 3rd edition, volume 9, pages 275 et seq and volume 15, pages 712 et seq.

The reaction may be carried out with advantage as follows:

Amine and alcohol or ether are vaporized at a suitable temperature, mixed in a molar ratio of for example from 4:1 to 1:1 of alcohol to amine, or more simply an appropriate mixture is completely vaporized at an appropriately high temperature, the vapor mixture is passed over the catalyst and condensed after the reaction. An inert gaseous diluent, for example nitrogen, may also be present. Conversion of the amine is generally from 90 to 98% and the yield based on reacted amine reaches from 90 to 96% of theory at a space-time yield of from 200 to 600 g/l of reaction space per hour.

It is a particular advantage of the process that high yields and high space-time yields can be achieved in an unsophisticated apparatus under conditions which can be set up and maintained without trouble.

N-alkyl derivatives of cyclic imines are used for example as auxiliaries, as intermediates, as pharmaceuticals and as catalysts. Thus for example N-methylmorpholine is used as a rubber auxiliary and N-methylpiperazine is known as a psycho-pharmacologic drug.

The following Examples illustrate the invention.

EXAMPLE 1

An experimental apparatus which can easily be adapted for industrial scale operation consists of an electrically heated quartz tube having a diameter of 50 mm and a length of 40 cm and a quartz evaporator. The quartz tube is arranged vertically and contains a catalyst having a particle size of from 60 to 200 microns which consists of 90% by weight of silicon dioxide and 10% by weight of phosphoric acid, a specific surface area of 400 m$^2$/g (BET method) and a pore radius of from 15 to 100 Å units.

106 g per hour of a mixture of 40% by weight of morpholine and 60% by weight of methanol is evaporated at 160° C, passed at 200° C over 200 ml of fluidized catalyst and condensed in a downstream cooler. 105 g per hour of condensate is obtained which consists of N-methylmorpholine to the extent of 40.5%; this is equivalent to a conversion of 95% and a yield of 91% based on reacted morpholine. N-methylmorpholine is obtained in a purity of 99% by fractional distillation in a packed column having a length of 50 cm.

EXAMPLE 2

The experiment of Example 1 is repeated but; instead of an hourly amount of 106 g, 240 g per hour is passed over the catalyst at 280° C. Conversion is again 95% and the yield of N-methylmorpholine is 88% based on morpholine reacted. It will be seen from this variation in the experimental conditions that the reaction is fairly insensitive to changes in the reaction conditions.

EXAMPLE 3

50 g per hour of a mixture of 40% by weight of pyrrolidine and 60% by weight of methanol, which has been vaporized at 165° C, is reacted at 190° C in the apparatus described in Example 1. Conversion is 93% and the yield of N-methylpyrrolidine reaches 89% based on pyrrolidine reacted.

EXAMPLE 4

120 ml of a mixture of 57% by weight of piperazine and 43% by weight of methanol is vaporized per hour at 160° C and passed at 220° C through the fluidized bed described in Example 1.

The conversion of piperazine is 49.3%. The ratio by weight of N-methylpiperazine to N,N'-dimethylpiperazine is 81:15. The yield of the two derivatives is 93% in all.

EXAMPLE 5

The procedure described in Example 4 is followed but 60 ml of the aforesaid mixture is used instead of 120 ml and it is passed at 180° C over the catalyst. At a conversion of 34%, the proportion of monoalkylated piperazine is 92% and dialkylated 8%. The total yield is 95% based on reacted piperazine.

We claim:

1. In a process for the production of an N-alkylated cyclic amine of the formula

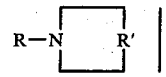

wherein R is an alkyl radical selected from the group consisting of methyl, ethyl and isopropyl, by reacting in the gas phase at a temperature of from 150° to 350° C an alcohol selected from the group consisting of methanol, ethanol and isopropanol or an ether selected from the group consisting of dimethyl ether, diethyl ether and diisopropyl ether with a cyclic amine of the formula

said latter amine being selected from the group consisting of pyrrolidine, 1-methylimidazolidine, oxazolidine, thiazolidine, dihydroisoindole, piperidine, 3-propylpiperidine, piperazine, N-methylpiperazine, perhydro-(1,3)-oxazine, perhydro-(1,3)-thiazine, hexamethylenimine, perhydrothiazepine, decamethylenimine, 3,5-dimethylmorpholine, and morpholine, in the presence of a catalyst containing a phosphorus compound on a carrier, the improvement which comprises carrying out said reaction in the presence of a silicon dioxide catalyst having a specific surface area of from 50 to 500 m²/g and containing from 0.1 to 20% by weight of phosphoric acid, said catalyst being obtained by converting an aqueous colloidal sodium silicate solution by addition of sulfuric acid to a silicic acid hydrogel, desalting said hydrogel with ammoniacal water, adding oxalic acid and an appropriate amount of phosphoric acid, milling the mixture so obtained until peptization takes place and spray drying to give a particulate powder.

2. A process as set forth in claim 1, wherein the catalyst has been obtained by spray drying with smoke gas.

3. A process as set forth in claim 1 whrein the compound of the formula

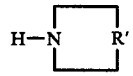

reacted is morpholine, 3,5-dimethylmorpholine, piperazine, hexamethylenimine or pyrrolidine.

4. A process as set forth in claim 1 wherein the catalyst is a fluidized bed catalyst having an average particle size of from 60 to 1000 microns.

* * * * *